(12) United States Patent
Villoing et al.

(10) Patent No.: US 7,279,167 B2
(45) Date of Patent: Oct. 9, 2007

(54) INFECTIOUS SALMON ANAEMIA VIRUS VACCINE

(75) Inventors: Stephane Villoing, Bergen (NO); Eirik Biering, Bergen (NO)

(73) Assignee: Intervet International B.V., Boxmeer (NL)

( * ) Notice: Subject to any disclaimer, the term of this patent is extended or adjusted under 35 U.S.C. 154(b) by 2 days.

(21) Appl. No.: 10/493,208

(22) PCT Filed: Oct. 16, 2002

(86) PCT No.: PCT/EP02/11552

§ 371 (c)(1),
(2), (4) Date: Apr. 20, 2004

(87) PCT Pub. No.: WO03/035680

PCT Pub. Date: May 1, 2003

(65) Prior Publication Data

US 2004/0253580 A1      Dec. 16, 2004

(30) Foreign Application Priority Data

Oct. 19, 2001   (EP) .................................. 01203951

(51) Int. Cl.
*A61K 39/12*     (2006.01)
*A61K 39/135*   (2006.01)

(52) U.S. Cl. .............................. 424/204.1; 424/186.1; 424/209.1; 536/23.72

(58) Field of Classification Search ............. 424/186.1, 424/209.1
See application file for complete search history.

(56) References Cited

FOREIGN PATENT DOCUMENTS

| EP | 1 094 069 | 4/2004 |
|----|-----------|--------|
| WO | 02 079231 | 10/2002 |

OTHER PUBLICATIONS

Clouthier, Sharon C et al: "Genomic organization of infectious salmon anaemia virus."; Journal of General Virology, vol. 83, No. 2, Feb. 2002; pp. 421-428.

Falk, Knut et al: "Characterization of infectious salmon anemia virus, an orthomyxo-like virus isolated from Atlantic salmon (Salmo salar L.)." Journal of Virology, vol. 71, No. 12, Dec. 1997, pp. 9016-9023.

Kibenge, Frederick S B et al: "Growth of infectious salmon anaemia virus in CHSE-214 cells and evidence for phenotypic difference virus strains."; Journal of General Virology, vol. 81, No. 1, Jan. 2000, p. 143-150.

Mjaaland, S et al: "Genomic characterization of the virus causing infectious salmon (Salmo salar L.): An orthomyxo-like virus in a teleost."; Journal of General Virology, vol. 71, No. 10, 1997, pp. 7681-7686.

Falk et al: "Characterization and applications of a monoclonal antibody against infectious salmon anaemia virus"; Diseases of Aquatic Organisms, vol. 34, No. 2, Oct. 1998, pp. 77-85.

Accession No. AF429988 of European Molecular Biology Laboratory—European Bioinformatics Institutes's Nucleotide Sequence Database, Oct. 25, 2002.

*Primary Examiner*—Stacy B. Chen
(74) *Attorney, Agent, or Firm*—Aaron L. Schwartz; William M. Blackstone

(57) ABSTRACT

This invention relates to Infectious Salmon Anaemia Virus (ISAV) antigenic polypeptides and nucleic acid molecules encoding them, as well as vaccines, transformed cells and transgenic fish. The antigenic polypeptides are able to elicit an immune response in immunized animals.

21 Claims, 2 Drawing Sheets

INFECTIOUS SALMON ANAEMIA VIRUS VACCINE

Figure 1:
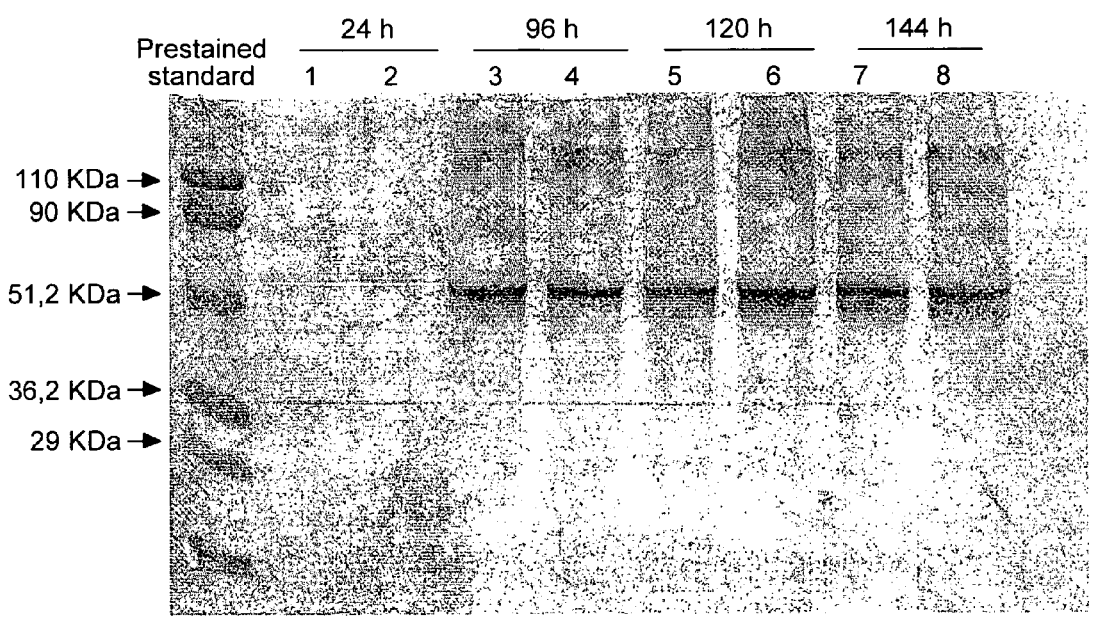

The material saved on two identical compact discs (COPY 1 and COPY 2) under the file name "Substitute Sequence Listing," created on Mar. 22, 2006, having a size of 11 KB is hereby incorporated by reference.

The present invention relates to a nucleic acid sequence encoding a viral protein and to DNA fragments, recombinant DNA molecules, live recombinant carriers and host cells comprising this nucleic acid sequence, to a protein encoded by this sequence, to vaccines comprising this protein or antibodies against his protein, to the use of said nucleic acid sequence, protein or antibodies for diagnostic or vaccination purposes and to diagnostic kits comprising the nucleic acid, protein or antibodies.

Infectious Salmon Anaemia (ISA) is a disease caused by a virus (ISAV) that belongs to the family Orthomyxoviridae. The disease is characterised by severe anaemia, leucopenia, ascites, haemorrhagic liver necrosis and petecchia of the vicera. The gills are pale, and petecchia of the skin is also common. The spleen is dark and swollen (Speilberg et al, 1995; Veterinary Pathology, 32, pp. 466-478). The virus replicates in endothelial cells, both in blood vessels and in the heart, and in polymorphonuclear leukocytes. Budding of the virus from pillar cells in the gills has been observed, indicating that gills are probably an important portal of entrance for ISAV.

ISA was observed for the first time in Norway (Thorud et al., 1988; Bull. Eur. Ass. Fish Pathol., 8 (5), pp. 109-111) and severe outbreaks have recently been diagnosed also in Scotland, the Shetland Islands and Canada. Mortality during outbreaks varies between 10 and 100% and younger individuals appear to be more susceptible than older. However, high mortality has also been observed among market size fish. Clinical outbreaks have been observed so far in Atlantic salmon, but rainbow trout and brown trout may act as carriers of the agent without developing clinical signs. Despite stamping out strategies, new outbreaks occur regularly and result in significant losses.

Control of the Disease Therefore has a High Priority.

It is an objective of the present invention to provide vaccines for combating Infectious Salmon Anaemia virus (ISAV) infections.

A new open reading frame of the viral genome has now surprisingly been found, which is thought to encode a novel viral protein. This protein turns out to be a suitable vaccine component in vaccines for combating ISAV infections. The gene encoding this protein has now been cloned and sequenced and the sequence is depicted in SEQ ID NO: 1. The Open Reading Frame consists of 1335 nucleotides. The ORF codes for a protein of 444 amino acids as depicted in SEQ ID NO 2. The protein has a molecular weight of 48 kD (+/−3 kD).

It is well-known in the art, that many different nucleic acid sequences can encode one and the same protein. This phenomenon is commonly known as wobble in the second and especially the third base of each triplet encoding an amino acid. This phenomenon can result in a heterology of about 30% for two nucleic acid sequences still encoding the same protein. Therefore, two nucleic acid sequences having a sequence homology of about 70% can still encode one and the same protein.

Thus, one embodiment relates to nucleic acid sequences encoding an 48 kD ISAV protein and to parts of those nucleic acid sequences that encode an immunogenic fragment of that protein, wherein those nucleic acid sequences or those parts thereof that encode an immunogenic fragment of that protein have a level of homology with the nucleic acid sequence of SEQ ID NO: 1 of at least 70%.

Preferably, the nucleic acid sequences encoding this 48 kD ISAV protein or the parts of that nucleic acid sequence that encode an immunogenic fragment of that protein have at least 80%, preferably 90%, more preferably 95% homology with the nucleic acid sequence of SEQ ID NO: 1. Even more preferred is a homology level of 98%, 99% or even 100%.

Nucleotide sequences that are complementary to the sequence depicted in SEQ ID NO 1 or nucleotide sequences that comprise tandem arrays of the sequences according to the invention are also within the scope of the invention.

The level of nucleotide homology can be determined with the computer program "BLAST 2 SEQUENCES" by selecting sub-program: "BLASTN" that can be found at the United States' National Institutes of Health's National Library of Medicine's National Center for Biotechnology Information world wide web site. A reference for this program is Tatiana A. Tatusova, Thomas L. Madden FEMS Microbiol. Letters 174: 247-250 (1999). Parameters used are the default parameters:

Reward for a match: +1. Penalty far a mismatch: −2. Open gap: 5. Extension gap: 2. Gap x_dropoff: 50.

Also, one form of this embodiment of the invention relates to nucleic acid sequences encoding an 48 kD ISAV protein or an immunogenic fragment of that protein comprising an amino acid sequence that has a homology of at least 70%, preferably 80%, 90%, 95%, 98% or even 100% with the amino acid sequence depicted in SEQ DE NO: 2.

Since the present invention discloses nucleic acid sequences encoding a novel 48 kD ISAV protein, it is now for the first time possible to obtain this protein in sufficient quantities. This can e.g. be done by using expression systems to express the whole or parts of the gene encoding the protein.

Therefore, in a more preferred form of this embodiment, the invention relates to DNA fragments comprising a nucleic acid sequence according to the invention. A DNA fragment is a stretch of nucleotides that functions as a carrier for a nucleic acid sequence according to the invention. Such DNA fragments can e.g. be plasmids, into which a nucleic acid sequence according to the invention is cloned. Such DNA fragments are e.g. useful for enhancing the amount of DNA for use as a primer and for expression of a nucleic acid sequence according to the invention, as described below.

An essential requirement for the expression of the nucleic acid sequence is an adequate promoter functionally linked to the nucleic acid sequence, so that the nucleic acid sequence is under the control of the promoter. It is obvious to those skilled in the art that the choice of a promoter extends to any eukaryotic, prokaryotic or viral promoter capable of directing gene transcription in cells used as host cells for protein expression.

Therefore, an even more preferred form of this embodiment relates to a recombinant DNA molecule comprising a DNA fragment and/or a nucleic acid sequence according to the invention wherein the nucleic acid sequence according to the invention is placed under the control of a functionally linked promoter. This can be obtained by means of e.g. standard molecular biology techniques. (Maniatis/Sambrook (Sambrook, J. Molecular cloning: a laboratory manual, 1989. ISBN 0-87969-309-6).

Functionally linked promoters are promoters that are capable of controlling the transcription of the nucleic acid sequences to which they are linked.

Such a promoter can be the native promoter of the novel gene or another promoter of the ISA Virus, provided that that promoter is functional in the cell used for expression. It can also be a heterologous promoter. When the host cells are bacteria, useful expression control sequences which may be used include the Trp promoter and operator (Goeddel, et al., Nucl. Acids-Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 4677-4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of vertebrate origin illustrative useful expression control sequences include the (human) cytomegalovirus immediate early promoter (Seed, B. et al., Nature 329, 840-842, 1987; Fynan, E. F. et al., PNAS 90, 11478-11482,1993; Ulmer, J. B. et al., Science 259, 1745-1748, 1993), Rous sarcoma virus LTR (RSV, Gorman, C. M. et al., PNAS 79, 6777-6781, 1982; Fynan et al., supra; Ulmer et al., supra), the MPSV LTR (Stacey et al., J. Virology 50, 725-732, 1984), SV40 immediate early promoter (Sprague J. et al., J. Virology 45, 773,1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992). The regulatory sequences may also include terminator and poly-adenylation sequences. Amongst the sequences that can be used are the well known bovine growth hormone poly-adenylation sequence, the SV40 poly-adenylation sequence, the human cytomegalovirus (hCMV) terminator and poly-adenylation sequences.

Bacterial, yeast, fungal, insect and vertebrate cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are attractive expression systems. Such systems are e.g. described in the French Patent Application with Publication number 2 714 074, and in U.S. NTIS Publication No U.S. No. 08/043,109 (Hoffman, S. and Rogers, W.: Public. Date 1 Dec. 1993).

A still even more preferred form of this embodiment of the invention relates to Live Recombinant Carriers (LRCs) comprising a nucleic acid sequence encoding the 48 kD protein or an immunogenic fragment thereof according to the invention, a DNA fragment according to the invention or a recombinant DNA molecule according to the invention. These LRCs are micro-organisms or viruses in which additional genetic information, in this case a nucleic acid sequence encoding the 48 kD protein or an immunogenic fragment thereof according to the invention has been cloned. Fish infected with such LRCs will produce an immunological response not only against the immunogens of the carrier, but also against the immunogenic parts of the protein(s) for which the genetic code is additionally cloned into the LRC, e.g. the novel ISAV gene according to the invention.

As an example of bacterial LRCs, bacteria such as *Vibrio anguillarum* known in the art can attractively be used. (Singer, J. T. et al., New Developments in Marine Biotechnology, p. 303-306, Eds. Le Gal and Halvorson, Plenum Press, New York, 1998).

Also, LRC viruses may be used as a way of transporting the nucleic acid sequence into a target cell. Viruses suitable for this task are e.g. alphavirus-vectors. A review on alphavirus-vectors is given by Sondra Schlesinger and Thomas W. Dubensky Jr. (1999) *Alphavirus vectors for gene expression and vaccines. Current opinion in Biotechnology*, 10:434-439.

The technique of in vivo homologous recombination, well-known in the art, can be used to introduce a recombinant nucleic acid sequence into the genome of a bacterium, parasite or virus of choice, capable of inducing expression of the inserted nucleic acid sequence according to the invention in the host animal.

Finally another form of this embodiment of the invention relates to a host cell comprising a nucleic acid sequence encoding a protein according to the invention, a DNA fragment comprising such a nucleic acid sequence or a recombinant DNA molecule comprising such a nucleic acid sequence under the control of a functionally linked promoter. This form also relates to a host cell containing a live recombinant carrier comprising a nucleic acid molecule encoding a 48 kD protein or an immunogenic fragment thereof according to the invention.

A host cell may be a cell of bacterial origin, e.g. *Escherichia coli, Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Another embodiment of the invention relates to the novel protein; the 48 kD ISAV protein and to immunogenic fragments thereof according to the invention.

The concept of immunogenic fragments will be defined below.

One form of this embodiment relates i.a. to 48 kD ISAV proteins and to immunogenic fragments thereof, that have an amino acid sequence that is at least 70% homologous to the amino acid sequence as depicted in SEQ ID NO: 2.

In a preferred form, the embodiment relates to such ISAV proteins and immunogenic fragments thereof, that have a sequence homology of at least 80%, preferably 90%, more preferably 95% homology to the amino acid sequence as depicted in SEQ ID NO: 2.

Even more preferred is a homology level of 98%, 99% or even 100%.

Another form of this embodiment relates to such 48 kD ISAV proteins and immunogenic fragments of said protein encoded by a nucleic acid sequence according to the invention.

The level of protein homology can be determined with the computer program "BLAST 2 SEQUENCES" by selecting sub-program: "BLASTP", that can be found at the United States' National Institutes of Health's National Library of Medicine's National Center for Biotechnology Information world wide web site. A reference for this program is Tatiana A. Tatusova, Thomas L. Madden FEMS Microbiol. Letters 174: 247-250(1999). Matrix used: "biosum62". Parameters used are the default parameters: Open gap: 11. Extension gap: 1. Gap x_dropoff: 50.

It will be understood that, for the particular proteins embraced herein, natural variations can exist between individual ISAV strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting proteins retain their immune reactivity.

This explains why ISAV proteins according to the invention, when isolated from different field isolates, may have homology levels of about 70%, while still representing the same protein with the same immunological characteristics.

Those variations in the amino acid sequence of a certain protein according to the invention that still provide a protein capable of inducing an immune response against infection with ISAV or at least against the clinical manifestations of the infection are considered as "not essentially influencing the immunogenicity".

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in a vertebrate host, i.e. comprises a B- or T-cell epitope. Shortly, an immunogenic fragment is a fragment that is capable of inducing antibodies that react with the full length protein, i.e. the 48 kD ISAV protein according to the invention. At this moment, a variety of techniques is available to easily identify DNA fragments encoding antigenic fragments (determinants). The method described by Geysen et al (Patent Application WO 84/03564, Patent Application WO 86/06487, U.S. Pat. No. 4,833,092, Proc. Natl. Acad. Sci. 81: 3998-4002 (1984), J. Imm. Meth. 102, 259-274 (1987), the so-called PEPSCAN method is an easy to perform, quick and well-established method for the detection of epitopes; the immunologically important regions of the protein. The method is used worldwide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47: 45-148 (1987) and U.S. Pat. No. 4,554, 101). T-cell epitopes can likewise be predicted from the sequence by computer with the aid of Berzofsky's amphiphilicity criterion (Science 235, 1059-1062 (1987) and U.S. Patent application NTIS U.S. Ser. No. 07/005,885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzofsky for HIV-epitopes; The FASEB Journal 5:2412-2418 (1991).

Therefore, one form of still another embodiment of the invention relates to vaccines for combating ISAV infection, that comprise a protein or immunogenic fragments thereof, according to the invention as described above together with a pharmaceutically acceptable carrier.

Still another embodiment of the present invention relates to the protein according to the invention or immunogenic fragments thereof for use in a vaccine.

Still another embodiment relates to the use of a protein according to the invention or immunogenic fragments of that protein for the manufacturing of a vaccine for combating ISAV infections.

One way of making a vaccine according to the invention is by growing the infectious salmon anaemia virus in cell culture, followed by biochemical purification of the 48 kD protein or immunogenic fragments thereof, from the virus. This is however a very time-consuming way of making the vaccine.

It is therefore much more convenient to use the expression products of the gene encoding the 48 kD protein or immunogenic fragments thereof in vaccines. This is possible for the first time now because the nucleic acid sequence of the gene encoding the 48 kD protein is provided in the present invention.

Vaccines based upon the expression products of these genes can easily be made by admixing the protein according to the invention or immunogenic fragments thereof according to the invention with a pharmaceutically acceptable carrier as described below.

Alternatively, a vaccine according to the invention can comprise live recombinant carriers as described above, capable of expressing the protein according to the invention or immunogenic fragments thereof. Such vaccines, e.g. based upon a *Vibrio* carrier or a viral carrier e.g. an alphavirus vector have the advantage over subunit vaccines that they better mimic the natural way of infection of ISAV. Moreover, their self-propagation is an advantage since only low amounts of the recombinant carrier are necessary for immunisation.

Vaccines can also be based upon host cells as described above, that comprise the protein or immunogenic fragments thereof according to the invention.

All vaccines described above contribute to active vaccination, i.e. they trigger the host's defence system.

Alternatively, antibodies can be raised in e.g. rabbits or can be obtained from antibody-producing cell lines as described below. Such antibodies can then be administered to the fish. This method of vaccination, passive vaccination, is the vaccination of choice when an animal is already infected, and there is no time to allow the natural immune response to be triggered. It is also the preferred method for vaccinating animals that are prone to sudden high infection pressure. The administered antibodies against the protein according to the invention or immunogenic fragments thereof can in these cases bind directly to ISAV and to cells exposing the ISAV protein according to the invention due to infection with ISAV. This has the advantage that it decreases or stops ISAV replication.

Therefore, one other form of this embodiment of the invention relates to a vaccine for combating ISAV infection that comprises antibodies against the ISAV protein according to the invention or an immunogenic fragment of that protein, and a pharmaceutically acceptable carrier.

Still another embodiment of this invention relates to antibodies against the ISAV protein according to the invention or an immunogenic fragment of that protein.

Methods for large-scale production of antibodies according to the invention are also known in the art. Such methods rely on the cloning of (fragments of) the genetic information encoding the protein according to the invention in a filamentous phage for phage display. Such techniques are described in review papers by Cortese, R. et al., (1994) in Trends Biotechn. 12: 262-267., by Clackson, T. & Wells, J. A. (1994) in Trends Biotechn. 12: 173-183, by Marks, J. D. et al., (1992) in J. Biol. Chem. 267: 16007-16010, by Winter, G. et al., (1994) in Annu. Rev. Immunol. 12; 433-455, and by Little, M. et al., (1994) Biotechn. Adv. 12: 539-555. The phages are subsequently used to screen camelid expression libraries expressing camelid heavy chain antibodies. (Muyldermans, S. and Lauwereys, M., Journ. Molec. Recogn. 12: 131-140 (1999) and Ghahroudi, M. A. et al., FEBS Letters 414: 512-526 (1997)). Cells from the library that express the desired antibodies can be replicated and subsequently be used for large scale expression of antibodies.

Still another embodiment relates to a method for the preparation of a vaccine according to the invention that comprises the admixing of antibodies according to the invention and a pharmaceutically acceptable carrier.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20-26 (1993)). This way of vaccination is also attractive for the vaccination of fish against ISAV infection. Therefore, still other forms of this embodiment of the invention relate to vaccines comprising nucleic acid sequences encoding a protein according to the invention or immunogenic fragments thereof, and to vaccines comprising DNA fragments that comprise such nucleic acid sequences.

Examples of DNA plasmids that are suitable for use in a DNA vaccine according to the invention are conventional cloning or expression plasmids for bacterial, eukaryotic and yeast host cells, many of said plasmids being commercially available. Well-known examples of such plasmids are pBR322 and pcDNA3 (Invitrogen). The DNA fragments or recombinant DNA molecules according to the invention should be able to induce protein expression of the nucleotide sequences. The DNA fragments or recombinant DNA molecules may comprise one or more nucleotide sequences according to the invention. In addition, the DNA fragments or recombinant DNA molecules may comprise other nucleotide sequences such as the immune-stimulating oligonucleotides having unmethylated CpG di-nucleotides, or nucleotide sequences that code for other antigenic proteins or adjuvating cytokines.

The nucleotide sequence according to the present invention or the DNA plasmid comprising a nucleotide sequence according to the present invention, preferably operably linked to a transcriptional regulatory sequence, to be used in the vaccine according to the invention can be naked or can be packaged in a delivery system. Suitable delivery systems are lipid vesicles, iscoms, dendromers, niosomes, polysaccharide matrices and the like, (see further below) all well-known in the art. Also very suitable as delivery system are attenuated live bacteria such as *Vibrio* species, and attenuated live viruses such as alphavirus vectors, as mentioned above.

Still other forms of this embodiment relate to vaccines comprising recombinant DNA molecules according to the invention.

DNA vaccines can easily be administered through intradermal application e.g. using a needle-less injector. This way of administration delivers the DNA directly into the cells of the animal to be vaccinated. Amounts of DNA in the range between 10 pg and 1000 μg provide good results. Preferably, amounts in the microgram range between 1 and 100 μg are used. Alternatively, animals can be dipped in solutions comprising e.g. between 10 pg and 1000 μg per ml of the DNA to be administered.

In a further embodiment, the vaccine according to the present invention additionally comprises one or more antigens derived from fish pathogenic organisms and viruses, antibodies against those antigens or genetic information encoding such antigens.

Of course, such antigens can be e.g. other ISAV antigens, such as the ISAV haemagglutinin. It can also be an antigen selected from other fish pathogenic organisms and viruses. Such organisms and viruses are preferably selected from the group of aquatic birnaviruses such as infectious pancreatic necrosis virus (IPNV), aquatic nodaviruses such as striped jack nervous necrosis virus (SJNNV), aquatic rhabdoviruses such as infectious haematopoietic necrosis virus (TV) and viral haemorrhagic septicaemia virus (VHSV), Pancreas Disease virus (SPDV) and aquatic orthomyxoviruses such as infectious salmon anaemia virus (ISAV) and the group of fish pathogenic bacteria such as *Flexibacter columnaris, Edwardsialla ictaluri, E. tarda, Yersinia ruckeri, Pasturella piscicida, Vibrio anguillarum, Aeromonas salmonicida* and *Renibacterium salmoninarum*

Vaccines based upon the 48 kD ISAV protein are also very suitable as marker vaccines. A marker vaccine is a vaccine that allows to discriminate between vaccinated and field-infected fish e.g. on the basis of a characteristic antibody panel, different from the antibody panel induced by wild type infection. A different antibody panel is induced e.g. when an immunogenic protein present on a wild type virus is not present in a vaccine: the host will then not make antibodies against that protein after vaccination. Thus, a vaccine based upon the 48 kD ISAV protein according to the invention would only induce antibodies against the 48 kD protein, whereas a vaccine based upon a live wild-type, live attenuated or inactivated whole ISA virus would induce antibodies against all or most of the viral proteins, such as i.a. the nucleoprotein.

A simple ELISA test, having wells comprising e.g. the purified recombinant nucleoprotein and wells comprising only purified 48 kD ISAV protein suffices to test antiserum from fish and to tell if the fish are either vaccinated with the 48 kD protein vaccine or suffered from ISAV field infection.

Merely as an example: a very suitable marker vaccine according to the invention comprises the 48 kD ISAV protein according to the invention in a combination with the ISAV haemagglutinin, and does explicitly not comprise the ISAV nucleoprotein. A diagnostic test for the diagnosis of field infection would then comprise the ISAV nucleoprotein. The combination of such a vaccine and diagnostic test is very suitable for the discrimination between vaccinated, infected and non-infected fish.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a protein or an immunogenic fragment thereof, according to the invention and/or antibodies against that protein or an immunogenic fragment thereof, and/or a nucleic acid sequence and/or a DNA fragment, a recombinant DNA molecule, a live recombinant carrier or host cell according to the invention, and a pharmaceutically acceptable carrier.

Vaccines according to the present invention may in a preferred presentation also contain an immunostimulatory substance, a so-called adjuvant Adjuvants in general comprise substances that boost the immune response of the host in a non-specific manner. A number of different adjuvants are known in the art. Examples of adjuvants frequently used in fish and shellfish farming are muramyldipeptides, lipopolysaccharides, several glucans and glycans and Carbopol® (a homopolymer). An extensive overview of adjuvants suitable for fish and shellfish vaccines is given in the review paper by Jan Raa (Reviews in Fisheries Science 4(3): 229-288 (1996)).

The vaccine may also comprise a so-called "vehicle". A vehicle is a compound to which the protein adheres, without being covalently bound to it. Such vehicles are i.a biomicrocapsules, micro-alginates, liposomes and macrosols, all known in the art.

A special form of such a vehicle, in which the antigen is partially embedded in the vehicle, is the so-called ISCOM (EP 109.942, EP 180.564, EP 242.380)

In addition, the vaccine may comprise one or more suitable surface-active compounds or emulsifiers, e.g. Span or Tween.

Often, the vaccine is mixed with stabilisers, e.g. to protect degradation-prone proteins from being degraded, to enhance the shelf-life of the vaccine, or to improve freeze-drying efficiency. Useful stabilisers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent.

It goes without saying, that other ways of adjuvating, adding vehicle compounds or diluents, emulsifying or stabilising a protein are also embodied in the present invention.

Vaccines according to the invention that are based upon the protein according to the invention or immunogenic fragments thereof can very suitably be administered in amounts ranging between 1 and 100 micrograms of protein per animal, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for respectively bacteria and viruses.

Many ways of administration, all known in the art can be applied. The vaccines according to the invention are preferably administered to the fish via injection, immersion, dipping or per oral. The administration protocol can be optimised in accordance with standard vaccination practice. Preferably the vaccine is administered via immersion or per oral, especially in case of commercial aqua culture farms.

For oral administration the vaccine is preferably mixed with a suitable carrier for oral administration i.e. cellulose, food or a metabolisable substance such as alpha-cellulose or different oils of vegetable or animals origin. Also an attractive is administration of the vaccine to high concentrations of live-feed organisms, followed by feeding the live-feed organisms to the target animal, e.g. the fish. Particularly preferred food carriers for oral delivery of the vaccine according to the invention are live-feed organism which are able to encapsulate the vaccine.

As mentioned above, lethality after virus infection can be up to 100%. Therefore, for efficient protection against disease, a quick and correct diagnosis of ISAV infection is important.

Therefore it is another objective of this invention to provide diagnostic tools suitable for the detection of ISAV infection.

The nucleic acid sequences, the proteins and the antibodies according to the invention are also suitable for use in diagnostics.

Therefore, another embodiment of the invention relates to nucleic acid sequences, proteins and antibodies according to the invention for use in diagnostics.

The nucleic acid sequences or fragments thereof can be used to detect the presence of ISAV in fish. A sample of fish infected with ISAV will comprise nucleic acid material derived from said virus, including nucleic acid sequences encoding for the protein according to the invention. These protein-encoding nucleic acid sequences will hybridise with a nucleic acid sequence according to the invention. Suitable methods for the detection of nucleic acid sequences that are reactive with the nucleic acid sequences of the present invention include hybridisation techniques including but not limited to PCR techniques and NASBA techniques. Thus the nucleic acid sequences according to the invention, in particular the sequences depicted in SEQ ID NO 1 can be used to prepare probes and primers for use in PCR and or NASBA techniques.

A diagnostic test kit for the detection of ISAV may e.g. comprise tools to enable the reaction of viral nucleic acid isolated from the fish to be tested with these tools Such tools are e.g. specific probes or (PCR-) primers, also referred to as primer fragments, based upon the nucleic acid sequences according to the invention. If genetic material of ISAV is present in the animal, this will e.g. specifically bind to specific PCR-primers and, e.g. after cDNA synthesis, will subsequently become amplified in PCR-reaction. The PCR-reaction product can then easily be detected in DNA gel electrophoresis.

The genetic material to be tested can most easily be isolated from the endothelial cells of leukocytes of the fish to be tested. Standard PCR-textbooks give methods for determining the length of the primers for selective PCR-reactions with ISAV DNA. Primer fragments with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in (Dieffenbach & Dreksler; PCR primers, a laboratory manual. ISBN 0-87969-447-5 (1995)).

Nucleic acid sequences according to the invention or primers of those nucleic acid sequences having a length of at least 12, preferably 15, more preferably 18, even more preferably 20, 22, 25, 30, 35 or 40 nucleotides in that order of preference, wherein the nucleic acid sequences or parts hereof have at least 70% homology with the nucleic acid sequence as depicted in SEQ ID NO: 1 are therefore also part of the invention. Primers are understood to have a length of at least 12 nucleotides and a homology of at least 70%, more preferably 80%, 85%, 90%, 95%, 98%, 99% or even 100%, in that order of preference, with the nucleic acid sequence as depicted in SEQ ID NO: 1. Such nucleic acid sequences can be used as primer fragments in PCR-reactions in order to enhance the amount of DNA that they encode or in hybridisation reactions. This allows the quick amplification or detection on blots of specific nucleotide sequences for use as a diagnostic tool for e.g. the detection of ISAV as indicated above.

Another test on genetic material is based upon growth of viral material obtained from the swab, followed by classical RNA purification followed (after optional cDNA synthesis) by classical hybridisation with radioactively or colour-labelled primer fragments. Colour-labelled and radioactively labelled fragments are generally called detection means. Both PCR-reactions and hybridisation reactions are well-known in the art and are i.a described in Maniatis/Sambrook (Sambrook, J. et al. Molecular cloning: a laboratory manual. ISBN 0-87969-309-6).

Thus, one embodiment of the invention relates to a diagnostic test kit for the detection of ISAV nucleic acid sequences. Such a test comprises a nucleic acid sequence according to the invention or a primer fragment thereof.

A diagnostic test kit based upon the detection of antigenic material of the specific 48 kD protein of ISAV and therefore suitable for the detection of ISAV infection may i.a comprise a standard ELISA test. In one example of such a test the walls of the wells of an ELISA plate are coated with antibodies directed against the 48 kD protein. After incubation with the material to be tested, labelled anti-ISAV antibodies are added to the wells. A colour reaction then reveals the presence of antigenic material from ISAV. Therefore, still another embodiment of the present invention relates to diagnostic test kits for the detection of antigenic material of ISAV. Such test kits comprise antibodies against an 48 kD ISAV protein or a fragment thereof according to the invention.

A diagnostic test kit based upon the detection in serum of antibodies against the specific 48 kD protein of ISAV and therefore suitable for the detection of ISAV infection may i.a. comprise a standard ELISA test. In such a test the walls of the wells of an ELISA plate can e.g. be coated with the 48 kD protein. After incubation with the material to be tested, labelled anti-48 kD antibodies are added to the wells. A lack of colour reaction then reveals the presence of antibodies against ISAV.

Therefore, still another embodiment of the present invention relates to diagnostic test kits for the detection of antibodies against ISAV. Such test kits comprise the 48 kD ISAV protein or a fragment thereof according to the invention.

The design of the immunoassay may vary. For example, the immunoassay may be based upon competition or direct reaction. Furthermore, protocols may use solid supports or may use cellular material. The detection of the antibody-antigen complex may involve the use of labelled antibodies; the labels may be, for example, enzymes, fluorescent-, chemiluminescent-, radio-active- or dye molecules.

Suitable methods for the detection of antibodies reactive with a protein according to the present invention in the sample include the enzyme-linked immunosorbent assay (ELISA), immunofluorescense test (IFT) and Western blot analysis.

The proteins or immunogenic fragments thereof according to the invention e.g. expressed as indicated above can be used to produce antibodies, which may be polyclonal, mono-specific or monoclonal (or derivatives thereof). If polyclonal antibodies are desired, techniques for producing and processing polyclonal sera are well-known in the art (e.g. Mayer and Walter, eds. *Immunochemical Methods in Cell and Molecular Biology*, Academic Press, London, 1987).

Monoclonal antibodies, reactive against the protein according to the invention or an immunogenic fragment thereof according to the present invention, can be prepared by immunising inbred mice by techniques also known in the art (Kohler and Milstein, *Nature*, 256, 495-497, 1975).

The following examples are illustrative for the invention and should not be interpreted as limitations of the invention.

EXAMPLES

Example 1

Virus Isolation and Construction of a cDNA Library

Kidney samples were taken from ISAV-infected Atlantic salmon (*Salmo salar*). Virus was isolated and propagated in Atlantic salmon kidney (ASK) cells as described by Devold et al. in Diseases of Aquatic Organisms 40: 9-18 (2000). RNA was isolated from ISAV-infected ASK cells using Trizol reagent (Life Technologies). RNA was isolated from these cells on days 2, 3 and 4 post-infection. RNA was pooled and mRNA was isolated using the Dynabeads mRNA Purification kit (Dynal). A sample of 2 µg mRNA was used for cDNA synthesis with the cDNA Synthesis Kit (Stratagene). A unidirectional bacteriophage Lambda cDNA library from ISAV infected ASK-cells was then constructed using the Uni-ZAP XR vector and Gigapack III Gold packaging extract (Stratagene).

Example 2

Cloning and Characterisation of ISAV Specific cDNA

Immunoscreening of the bacteriophage Lambda cDNA library was performed with an anti ISAV polyclonal rabbit serum using the picoBlue Immunoscreening Kit (Stratagene). Sequencing of positive clones identified a done comprising an ISAV genetic segment with an open reading frame (ORF) of 1335 bases. The clone was designated EB5, and database searches revealed no significant homology to other sequences. The viral origin of the cDNA sequence was demonstrated using PCR. EB5 specific PCR primers (5'-GGAGTGCCTGGAGGTGTA-3' (SEQ ID NO.: 3) and 5'-CCTCTGGTGGACATCCTCTG-3' (SEQ ID NO.: 4)) amplified a product from ISAV infected ASK cells and not from uninfected cells. To obtain a full-length cDNA sequence, 5' RACE was performed with the 5'RACE System, Version 2.0 (Life Technologies). RACE products were cloned into the pCR 2.1-TOPO vector using the TOPO TA Cloning Kit (Invitrogen) and sequenced.

Example 3

Use of ISAV Segment for RT-PCR Diagnostic

A primer set (ABCD and EFGH) targeted against the ISA virus genome segment according to the invention was constructed of which the sequences are given in Table 1.

TABLE 1

Sequence of the primers tested for use in RT-PCR amplification of the segment.

| Primer | Sequence | % GC | Tm (° C.) |
|---|---|---|---|
| EB5-1 | 5'-GGAGTGCTCCTGGAGGTGTA-3' (SEQ ID NO.: 3) | 60 | 71 |
| EB5-2 | 5'-CCTCTGGTGGACATCCTCTG-3' (SEQ ID NO.: 4) | 60 | 71 |

The RNA was extracted from Kidney tissues with Trizol (Life Technologies). About 1.5 µg total RNA+1.5 µl (1.5 µg) random hexamers (pd(N)$_6$) in a total volume of 10 µl were incubated at 70° C. for 5 minutes and then cooled to 4° C. RT-mix containing 5.0 µl 5×RT buffer+1.2 µl 200 mM DL-dithiothreitol (DTT)+2.5 µl 10 mM dNTP+0.5 µl RNasin (20 units/µl)+4.3 µl dH2O+1.5 µl (20 units/µl) Moloney Murine Leukemia Virus Reverse Transcriptase (MMLV-RT), were added at room temperature making a total of 25 µl. This solution was incubated at 37° C. for 60 minutes.

The PCR consisted of 2 µl of cDNA-solution that was added to 23 µl of reaction mixture consisting of 14.2 µl ddH$_2$O, 2.5 µl (×10) running buffer, 2.0 µl (25 mM MgCl), 2 µl dNTP (10 mM), 1.0 µl of each primer (20 µM), 0.3 µl (5 units/µl) Taq DNA polymerase (Pharmacia Biotech). The mixture was denatured at 94° C. for 3 minutes and amplification was performed with 35 cycles of 94° C. for 30 seconds, 65° C. for 45 seconds, and 72° C. for 90 seconds, followed by extension at 72° C. for 10 minutes. The tubes were then held at 4° C. Amplification and reverse transcription were performed in a thermal cycler with heated lid.

Aliquots (10 µl) of the PCR reaction mixture were electrophoresed in 1% agarose 1×TBE gel containing ethidium bromide stain (Gibco-BRL) and photographed under UV transillumination. A DNA ladder was applied to identify the size of the PCR products. In addition to RNA from fish that were not infected with ISA virus, negative controls containing H$_2$O instead of RNA or cDNA were used to test each reaction mixture.

Specificity.

The products from the RT-PCR gave the predicted size of 363 base pairs. The specificity of the primer set was determined by sequencing the PCR products using the BigDye Sequencing Kit and an ABI Prism 6700 sequencing machine (PE Biosystems). In the specificity tests of the ISA virus RT-PCR assay, using the sense and antisense primers, non-infected cells gave, as expected, no PCR amplification products.

Example 4

Expression of the 48 kD Protein in Baculovirus System and Immune Reactivity of the Expression Product The full length 48 kD gene from the Norwegian Bremnes ISAV strain has been subcloned in pFastBac.1 vector (In Vitrogen). Recombinant baculovirus BacSeg5 was so obtained.

A 50 ml SF9 culture (50.10$^6$ cells) has been infected with our BacSeg5 (MOI=0,1) and grown at 28° C. up to 6 days post infection. At sampling points 24 hours, 96 hours, 120 hours and 144 hours post infection, aliquots of 1 ml (×2 replicates) have been taken and centrifuged. The pelleted infected coils have been resuspended in 100 µl sample buffer 1×. 10 µl of these samples were then migrated on a 10% SDS-PAGE and analysed by Western-blot using anti-peptide serum, raised in rabbits, against peptides WTTSRSRLEDSTWQGG (amino acids 60-75 of SEQ ID NO.: 2) and FTTERIKTGKVDLDSC (amino acids 183-198 of SEQ ID NO.: 2). An anti-rabbit IgG secondary antibody coupled to horse raddish peroxidase was then used and enabled the detection of 48 kD protein. It turned out, that the 48 kD protein is found on SDS-PAGE gels to have a molecular weight of around 53 kD. Expression was maximum at 5 days post infection (120 hpi). FIG. 1 shows a Western blot of the expression results.

Example 5

Figure 2:
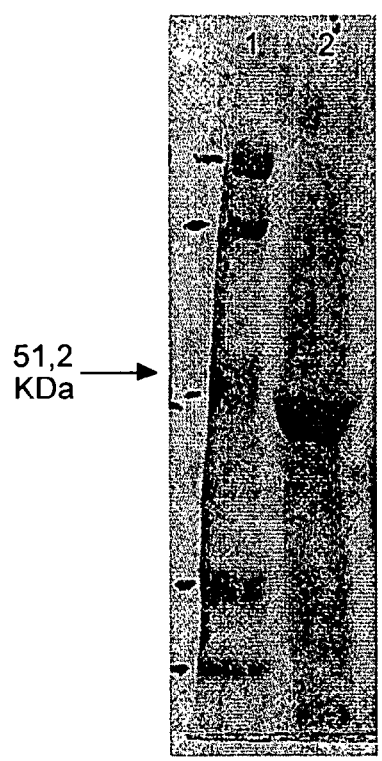

Expression of the 48 kD Protein in E. coli Rosetta BL21 (DE3) pLysS Cells System and Immune Reactivity of the Expression Product The 48 kD gene from the Norwegian Bremnes ISAV strain has been subcloned in pET30a vector (Novagen) and expressed in E. coli Rosetta BL21 (DE3) pLysS strain (Novagen). Different constructs have been made: the full length 48 kD gene (fullSeg5) and the gene without its transmembrane region (ΔSeg5). After IPTG induction (1 mM IPTG), aliquots of 1 ml induced Rosetta cells were taken at sampling points 0 hour post induction and 3 hours post induction. The cells pellet was resuspended in 150 µl 1× sampling buffer. Inclusion bodies were also prepared out of 50 ml culture of Rosetta cells carrying pET30a+ΔSeg5. These inclusion bodies were resuspended in 1 ml 1×PBS and 10 µl were then mixed with 5 µl 1× sampling buffer and migrated on a 10% SDS-PAGE for Coomassie staining (FIG. 2, lane 2) along with a prestained marker ((FIG. 2, lane 1).

Aliquots of 15 µl induced culture samples and inclusion bodies samples were also run on another 10% SDS-PAGE and analysed by Western-blot using anti-peptide serum as described above in Example 4. An anti-rabbit IgG secondary antibody coupled to horse raddish peroxidase was then used and enabled the detection of the 48 kD protein at the expected sizes. (FIG. 3, lane 1: prestained marker; lane 2: non induced ΔSeg5; lane 3: 3 hrs induced ΔSeg5; lane 4: 3 hrs induced ΔSeg5 inclusion bodies; lane 5: 3 hrs induced fullSeg5). Best expression levels were observed with ΔSeg5 construct.

Results: in conclusion, it is clear from Example 4 and 5 that the 48 kD protein can be efficiently expressed in both baculovirus expression systems and bacterial expression systems. Moreover, the immune reactivity of the protein is clearly shown in both FIGS. 1 and 3.

Legend to the figures:

FIG. 1: Western blot of the 48 kD protein according to the invention expressed in a baculosystem. See also Example 4.

FIG. 2: Coomassie stained SDS-PAGE gel of the 48 kD protein according to the invention expressed in a bacterial expression system. See also Example 5.

Figure 3:
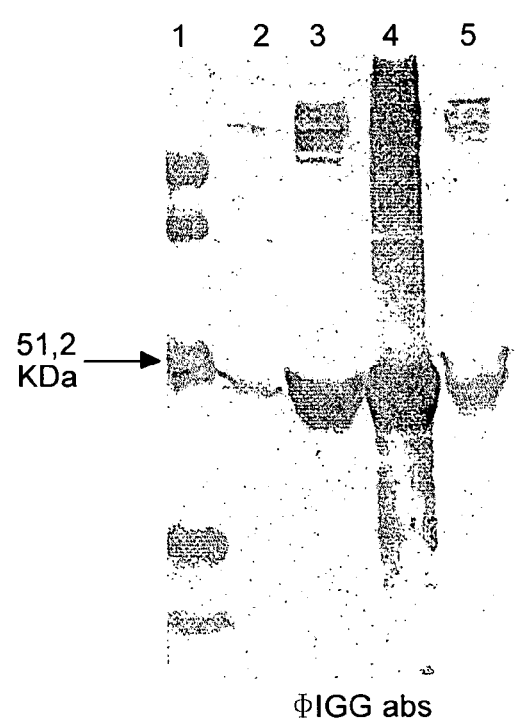

FIG. 3: Western blot of the 48 kD protein according to the invention expressed in a bacterial expression system. See also Example 5.

The invention claimed is:

1. An isolated nucleic acid sequence that encodes the Infectious Salmon Anaemia virus (ISAV) protein as depicted in SEQ ID NO: 2 or an immunogenic fragment of said protein;
    wherein said immunogenic fragment comprises amino acids 60-75 of SEQ ID NO: 2 or amino acids 183-198 of SEQ ID NO: 2.

2. The nucleic acid sequence according to claim 1, wherein the nucleic acid sequence is SEQ ID NO: 1.

3. A DNA fragment comprising a nucleic acid sequence according to claim 1.

4. A recombinant DNA molecule comprising a nucleic acid sequence according to claim 1 that is under the control of a functionally linked promoter.

5. A live recombinant carrier comprising a nucleic acid sequence according to claim 1.

6. A cultured transformed cell comprising a nucleic acid sequence according to claim 1.

7. An isolated Infectious Salmon Anaemia virus (ISAV) amino acid sequence comprising SEQ ID NO: 2 or an immunogenic fragment thereof;
    wherein said immunogenic fragment comprises amino acids 60-75 of SEQ ID NO: 2 or amino acids 183-198 of SEQ ID NO: 2.

8. A composition comprising a nucleic acid sequence according to claim 1 and a pharmaceutically acceptable carrier.

9. The composition according to claim 8, comprising an adjuvant.

10. The composition according to claim 8, further comprising nucleic acid encoding an additional antigen derived from a virus or micro-organism pathogenic to fish.

11. The composition according to claim 10, wherein the virus or micro-organism pathogenic to fish is selected from the group consisting of infectious pancreatic necrosis virus (IPNV), striped jack nervous necrosis virus (SJNNV), infectious haematopoietic necrosis virus (IHNV), viral haemorrhagic septicaemia virus (VHSV), Pancreas Disease virus (SPDV), infectious salmon anaemia virus (ISAV), *Flexibacter columnaris, Edwardsialla ictaluri, E. tarda, Yersinia ruckeri, Pasturella piscicida, Vibrio anguillarum, Aeromonas salmonicida* and *Renibacterium salmoninarum*.

12. A diagnostic kit comprising the nucleic acid sequence according to claim 1.

13. A composition comprising a protein or immunogenic fragment of said protein according to claim 7 and a pharmaceutically acceptable carrier.

14. The composition according to claim 13, comprising an adjuvant.

15. The composition according to claim 13, comprising an additional antigen derived from a virus or microorganism pathogenic to fish.

16. A diagnostic kit comprising the protein or fragment according to claim 7.

17. The composition of claim 7, wherein said amino acid sequence comprises SEQ ID NO: 2.

18. The composition of claim 7, wherein said amino acid sequence comprises amino acids 60-75 of SEQ ID NO: 2.

19. The composition of claim 7, wherein said amino acid sequence comprises amino acids 183-198 of SEQ ID NO: 2.

20. The nucleic acid sequence according to claim 1, wherein the nucleic acid sequence comprises nucleotides 178-225 of SEQ ID NO: 1.

21. The nucleic acid sequence according to claim 1, wherein the nucleic acid sequence comprises nucleotides 547-594 of SEQ ID NO: 1.

* * * * *

SEQUENCE LISTING

<160> NUMBER OF SEQ ID NOS: 2

<210> SEQ ID NO 1
<211> LENGTH: 1335
<212> TYPE: DNA
<213> ORGANISM: Infectious salmon anemia virus
<220> FEATURE:
<221> NAME/KEY: CDS
<222> LOCATION: (1)..(1332)

<400> SEQUENCE: 1

| | | | | | | | | | | | | | | | | |
|---|---|---|---|---|---|---|---|---|---|---|---|---|---|---|---|---|
| atg | gct | ttt | cta | aca | att | tta | gtc | ttg | ttc | ctt | ttg | aaa | gag | gtt | ctt | 48 |
| Met | Ala | Phe | Leu | Thr | Ile | Leu | Val | Leu | Phe | Leu | Leu | Lys | Glu | Val | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tgt | gag | cct | tgt | acc | tgt | gac | aac | cca | aca | tgt | cta | ggt | tta | aca | att | 96 |
| Cys | Glu | Pro | Cys | Thr | Cys | Asp | Asn | Pro | Thr | Cys | Leu | Gly | Leu | Thr | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| cct | agg | act | ggt | tat | gtt | agg | agt | gct | cct | gga | ggt | gta | cta | ttg | aca | 144 |
| Pro | Arg | Thr | Gly | Tyr | Val | Arg | Ser | Ala | Pro | Gly | Gly | Val | Leu | Leu | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| gag | acc | atc | acg | gaa | agc | cct | gct | ctg | gca | gaa | tgg | acc | act | tcc | cga | 192 |
| Glu | Thr | Ile | Thr | Glu | Ser | Pro | Ala | Leu | Ala | Glu | Trp | Thr | Thr | Ser | Arg | |
| 50 | | | | | 55 | | | | | 60 | | | | | | |

| | | | | | | | | | | | | | | | | |
|---|---|---|---|---|---|---|---|---|---|---|---|---|---|---|---|---|
| agc | aga | ctt | gag | gat | tcg | acg | tgg | cag | gga | gga | gag | gtc | aaa | agt | ggc | 240 |
| Ser | Arg | Leu | Glu | Asp | Ser | Thr | Trp | Gln | Gly | Gly | Glu | Val | Lys | Ser | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aaa | gtc | tcg | cag | acg | ttg | ttt | gaa | gca | atc | cag | ggc | acc | cag | atg | gag | 288 |
| Lys | Val | Ser | Gln | Thr | Leu | Phe | Glu | Ala | Ile | Gln | Gly | Thr | Gln | Met | Glu | |
| | | | | | 85 | | | | | 90 | | | | | 95 | |

| | | | | | | | | | | | | | | | | |
|---|---|---|---|---|---|---|---|---|---|---|---|---|---|---|---|---|
| aac | tgt | gca | gtg | aag | gct | gta | ttt | gat | act | tcc | ttt | gtg | aat | ctc | act | 336 |
| Asn | Cys | Ala | Val | Lys | Ala | Val | Phe | Asp | Thr | Ser | Phe | Val | Asn | Leu | Thr | |
| | | | | 100 | | | | | 105 | | | | | 110 | | |

| | | | | | | | | | | | | | | | | |
|---|---|---|---|---|---|---|---|---|---|---|---|---|---|---|---|---|
| cga | cat | gat | gtt | gtc | ctt | ggt | agg | gtg | aag | gtg | tct | cct | ttt | ggt | ggt | 384 |
| Arg | His | Asp | Val | Val | Leu | Gly | Arg | Val | Lys | Val | Ser | Pro | Phe | Gly | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| gag | cat | gac | atc | tcc | aaa | tgt | ggg | agg | aaa | gga | tta | aaa | gtt | ttc | atc | 432 |
| Glu | His | Asp | Ile | Ser | Lys | Cys | Gly | Arg | Lys | Gly | Leu | Lys | Val | Phe | Ile | |
| | | 130 | | | | | 135 | | | | | 140 | | | | |

| | | | | | | | | | | | | | | | | |
|---|---|---|---|---|---|---|---|---|---|---|---|---|---|---|---|---|
| tgc | gga | ggt | aca | aca | ggt | tat | gta | acc | aga | gga | tgt | cca | cca | gag | gaa | 480 |
| Cys | Gly | Gly | Thr | Thr | Gly | Tyr | Val | Thr | Arg | Gly | Cys | Pro | Pro | Glu | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tgc | agg | ggg | agg | aaa | gga | agg | atg | atg | tct | cta | gaa | cca | act | gca | gac | 528 |
| Cys | Arg | Gly | Arg | Lys | Gly | Arg | Met | Met | Ser | Leu | Glu | Pro | Thr | Ala | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| tgt | gga | gtg | gaa | aaa | ggc | ttt | aca | acg | gaa | agg | att | aag | act | gga | aag | 576 |
| Cys | Gly | Val | Glu | Lys | Gly | Phe | Thr | Thr | Glu | Arg | Ile | Lys | Thr | Gly | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| gtg | gac | tta | gat | agc | tgt | tgc | act | cag | cat | gga | tgt | aca | aaa | ggt | att | 624 |
| Val | Asp | Leu | Asp | Ser | Cys | Cys | Thr | Gln | His | Gly | Cys | Thr | Lys | Gly | Ile | |
| | | 195 | | | | | 200 | | | | | 205 | | | | |

| | | | | | | | | | | | | | | | | |
|---|---|---|---|---|---|---|---|---|---|---|---|---|---|---|---|---|
| agg | gtg | gag | gtt | cca | tcg | cct | gta | ctg | gta | tcg | gcc | aaa | tgc | aat | gaa | 672 |
| Arg | Val | Glu | Val | Pro | Ser | Pro | Val | Leu | Val | Ser | Ala | Lys | Cys | Asn | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| att | tca | ttc | aga | gta | gtg | ccg | ttc | cat | tct | gta | cca | gac | agg | cta | ggg | 720 |
| Ile | Ser | Phe | Arg | Val | Val | Pro | Phe | His | Ser | Val | Pro | Asp | Arg | Leu | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ttc | gct | aga | act | agt | tct | ttt | aca | cta | aga | gcc | aac | ctc | gct | aac | cag | 768 |
| Phe | Ala | Arg | Thr | Ser | Ser | Phe | Thr | Leu | Arg | Ala | Asn | Leu | Ala | Asn | Gln | |
| | | | | 245 | | | | | 250 | | | | | 255 | | |

-continued

```
cat gga tgg tct aaa tac agc ttc aac ctg aga gca ttc cca gga gaa    816
His Gly Trp Ser Lys Tyr Ser Phe Asn Leu Arg Ala Phe Pro Gly Glu
        260                 265                 270 gag ttc atc aaa tgc tgt gga ttt act ttg ggg atc gga ggt gct tgg    864
Glu Phe Ile Lys Cys Cys Gly Phe Thr Leu Gly Ile Gly Gly Ala Trp
275                 280                 285 ttt caa gct tat ttg aat gga gaa gtc caa gga gac ggt gca gca tcc    912
Phe Gln Ala Tyr Leu Asn Gly Glu Val Gln Gly Asp Gly Ala Ala Ser
290                 295                 300 gca gaa gat gtg aag gaa aaa ctg aac gga att ata gac cag atc aac    960
Ala Glu Asp Val Lys Glu Lys Leu Asn Gly Ile Ile Asp Gln Ile Asn
305                 310                 315                 320 aag gtg aac ctg ctg cta gaa gga gaa att gaa gca gtg aga aga att   1008
Lys Val Asn Leu Leu Leu Glu Gly Glu Ile Glu Ala Val Arg Arg Ile
                325                 330                 335 gcc tac atg aac caa gcc tca agt ctg cag aac caa gtg gag att gga   1056
Ala Tyr Met Asn Gln Ala Ser Ser Leu Gln Asn Gln Val Glu Ile Gly
            340                 345                 350 ctg ata ggg gaa tat ctg aac att agc agc tgg ttg gaa acc aaa aca   1104
Leu Ile Gly Glu Tyr Leu Asn Ile Ser Ser Trp Leu Glu Thr Lys Thr
        355                 360                 365 ttg acg aag aca gag gag ggt ctt atg aaa gac ggt tgg tgt cgg tct   1152
Leu Thr Lys Thr Glu Glu Gly Leu Met Lys Asp Gly Trp Cys Arg Ser
370                 375                 380 agc aat cat tgc tgg tgt cct cct ggt act gtt gga atc cct act ata   1200
Ser Asn His Cys Trp Cys Pro Pro Gly Thr Val Gly Ile Pro Thr Ile
385                 390                 395                 400 ggt tat gtc gac aat att aag gag gtg aca ggg acg agt tgg tgg atg   1248
Gly Tyr Val Asp Asn Ile Lys Glu Val Thr Gly Thr Ser Trp Trp Met
                405                 410                 415 gtg atg att cat tac att atc gtt gga ctg att gta gtt gtg ttg gtg   1296
Val Met Ile His Tyr Ile Ile Val Gly Leu Ile Val Val Val Leu Val
            420                 425                 430 gtg ctg gga ctt aag ctg tgg gga tgc att agg aga taa                1335
Val Leu Gly Leu Lys Leu Trp Gly Cys Ile Arg Arg
        435                 440
```

<210> SEQ ID NO 2
<211> LENGTH: 444
<212> TYPE: PRT
<213> ORGANISM: Infectious salmon anemia virus

<400> SEQUENCE: 2

```
Met Ala Phe Leu Thr Ile Leu Val Leu Phe Leu Leu Lys Glu Val Leu
1               5                   10                  15

Cys Glu Pro Cys Thr Cys Asp Asn Pro Thr Cys Leu Gly Leu Thr Ile
                20                  25                  30

Pro Arg Thr Gly Tyr Val Arg Ser Ala Pro Gly Gly Val Leu Leu Thr
            35                  40                  45

Glu Thr Ile Thr Glu Ser Pro Ala Leu Ala Glu Trp Thr Thr Ser Arg
        50                  55                  60

Ser Arg Leu Glu Asp Ser Thr Trp Gln Gly Gly Glu Val Lys Ser Gly
65                  70                  75                  80

Lys Val Ser Gln Thr Leu Phe Glu Ala Ile Gln Gly Thr Gln Met Glu
                85                  90                  95

Asn Cys Ala Val Lys Ala Val Phe Asp Thr Ser Phe Val Asn Leu Thr
            100                 105                 110

Arg His Asp Val Val Leu Gly Arg Val Lys Val Ser Pro Phe Gly Gly
        115                 120                 125
```

-continued

```
Glu His Asp Ile Ser Lys Cys Gly Arg Lys Gly Leu Lys Val Phe Ile
    130             135             140
Cys Gly Gly Thr Thr Gly Tyr Val Thr Arg Gly Cys Pro Pro Glu Glu
145             150             155             160
Cys Arg Gly Arg Lys Gly Arg Met Met Ser Leu Glu Pro Thr Ala Asp
                165             170             175
Cys Gly Val Glu Lys Gly Phe Thr Thr Glu Arg Ile Lys Thr Gly Lys
            180             185             190
Val Asp Leu Asp Ser Cys Cys Thr Gln His Gly Cys Thr Lys Gly Ile
        195             200             205
Arg Val Glu Val Pro Ser Pro Val Leu Val Ser Ala Lys Cys Asn Glu
    210             215             220
Ile Ser Phe Arg Val Val Pro Phe His Ser Val Pro Asp Arg Leu Gly
225             230             235             240
Phe Ala Arg Thr Ser Ser Phe Thr Leu Arg Ala Asn Leu Ala Asn Gln
                245             250             255
His Gly Trp Ser Lys Tyr Ser Phe Asn Leu Arg Ala Phe Pro Gly Glu
            260             265             270
Glu Phe Ile Lys Cys Cys Gly Phe Thr Leu Gly Ile Gly Gly Ala Trp
        275             280             285
Phe Gln Ala Tyr Leu Asn Gly Glu Val Gln Gly Asp Gly Ala Ala Ser
    290             295             300
Ala Glu Asp Val Lys Glu Lys Leu Asn Gly Ile Ile Asp Gln Ile Asn
305             310             315             320
Lys Val Asn Leu Leu Leu Glu Gly Glu Ile Glu Ala Val Arg Arg Ile
                325             330             335
Ala Tyr Met Asn Gln Ala Ser Ser Leu Gln Asn Gln Val Glu Ile Gly
            340             345             350
Leu Ile Gly Glu Tyr Leu Asn Ile Ser Ser Trp Leu Glu Thr Lys Thr
        355             360             365
Leu Thr Lys Thr Glu Glu Gly Leu Met Lys Asp Gly Trp Cys Arg Ser
    370             375             380
Ser Asn His Cys Trp Cys Pro Pro Gly Thr Val Gly Ile Pro Thr Ile
385             390             395             400
Gly Tyr Val Asp Asn Ile Lys Glu Val Thr Gly Thr Ser Trp Trp Met
                405             410             415
Val Met Ile His Tyr Ile Ile Val Gly Leu Ile Val Val Val Leu Val
            420             425             430
Val Leu Gly Leu Lys Leu Trp Gly Cys Ile Arg Arg
    435             440
```